US009585301B1

(12) United States Patent
Lund et al.

(10) Patent No.: US 9,585,301 B1
(45) Date of Patent: *Mar. 7, 2017

(54) AGRICULTURAL PLANTER WITH AUTOMATIC DEPTH AND SEEDING RATE CONTROL

(71) Applicant: Veris Technologies Inc., Salina, KS (US)

(72) Inventors: Eric Lund, Salina, KS (US); Chase Maxton, Salina, KS (US); Kyle Jensen, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 183 days.

This patent is subject to a terminal disclaimer.

(21) Appl. No.: 14/253,839

(22) Filed: Apr. 15, 2014

Related U.S. Application Data

(60) Provisional application No. 61/812,131, filed on Apr. 15, 2013.

(51) Int. Cl.
*A01C 5/06* (2006.01)
*A01C 7/10* (2006.01)
(Continued)

(52) U.S. Cl.
CPC .............. *A01C 5/064* (2013.01); *A01B 49/04* (2013.01); *A01B 49/06* (2013.01); *A01B 63/008* (2013.01); *A01C 7/102* (2013.01); *A01C 7/203* (2013.01)

(58) Field of Classification Search
CPC ....... A01B 33/087; A01B 35/32; A01B 49/04; A01B 49/00; A01B 49/06; A01B 63/008; A01B 63/002; A01B 63/00; A01C 21/007; A01C 5/064; A01C 5/062; A01C 5/06; A01C 5/00; A01C 7/102; A01C 7/10; A01C 7/08; A01C 7/00; A01C 7/203; A01C 7/201; A01C 7/20; A01G 25/167; G01N 2001/021;
(Continued)

(56) References Cited

U.S. PATENT DOCUMENTS

| 5,841,282 A * | 11/1998 | Christy ................ A01B 79/005 111/118 |
| 6,116,172 A * | 9/2000 | Prairie ..................... A01O 5/06 111/123 |
| 2012/0048160 A1* | 3/2012 | Adams .................... A01C 7/203 111/163 |

OTHER PUBLICATIONS

Adamchuk et al., "On-the-go soil sensors for precision agriculture", Computers and Electronics for Agriculture, No. 44, pp. 71-91, Jun. 12, 2004.*

* cited by examiner

*Primary Examiner* — Christopher J Novosad
(74) *Attorney, Agent, or Firm* — Jeffrey L. Thompson; Thompson & Thompson, P.A.

(57) ABSTRACT

An agricultural planter having sensors for measuring multiple soil properties adjusts planting depth and seeding rate in real time based on the measured soil properties. An optical module is carried by the planter for collecting soil reflectance data. A pair of soil contact blades protrude from or are embedded in the optical module for collecting soil EC data and soil moisture data. A switching circuit or phase lock loop allows the same soil contact blades to feed signals to both a soil EC signal conditioning circuit and a soil moisture signal conditioning circuit. The soil moisture data can be used to calibrate the soil EC data and the soil reflectance data to compensate for effects of changing soil moisture conditions across a field. The sensor module can be positioned behind a seed tube and used as a seed firmer, or incorporated into a seed tube guard.

18 Claims, 9 Drawing Sheets

(51) Int. Cl.
*A01C 7/20* (2006.01)
*A01B 49/06* (2006.01)
*A01B 63/00* (2006.01)
*A01B 49/04* (2006.01)

(58) Field of Classification Search
CPC ............. G01N 2033/245; G01N 21/55; G01N 27/223; G01N 21/31
See application file for complete search history.

AGRICULTURAL PLANTER WITH AUTOMATIC DEPTH AND SEEDING RATE CONTROL

RELATED APPLICATIONS

This application claims the benefit of U.S. Provisional Patent Application No. 61/812,131 filed on Apr. 15, 2013. The entire content of the priority application is incorporated herein by reference.

BACKGROUND OF THE INVENTION

Field of the Invention

The present invention relates generally to methods and systems for measuring multiple soil properties across a field, and to agricultural planters that vary seeding rates and planting depths on-the-go during planting operations.

Description of the Related Art

Soil moisture is a major driver of crop production, particularly in arid regions. Soil moisture varies spatially within fields due to soil texture, topography, crop usage, irrigation patterns, and various other variables.

Fixed, semi-permanent moisture sensors (e.g., gypsum blocks and neutron probes) and manually inserted sensors (e.g., TDR, capacitance) have been used for many years to monitor soil moisture levels in agricultural fields. However, these moisture sensors do not capture the spatial variability as their expense and manual deployment make it unfeasible to collect enough measurements to produce a spatially accurate map of soil moisture.

Variable rate irrigation allows limited irrigation water supplies to be applied at different rates in different areas of a field. For example, variable rate irrigation can be used to apply more irrigation water to zones of a field where water holding capacity is lower or where crop use or productivity is expected to be greater. Fixed moisture sensors are often used in fields with variable rate irrigation. However, the use of fixed moisture sensors does not link soil moisture with soil properties that affect water-holding capacity and crop usage of water.

Systems and methods are known for measuring soil electrical conductivity (EC) and soil color (reflectance). For example, the Applicant's copending application Ser. No. 13/277,208 filed on Oct. 19, 2011, for an invention titled "MOBILE SOIL OPTICAL MAPPING SYSTEM" provides a system for measuring soil reflectance values and using the soil reflectance data to determine and map soil organic matter (OM). For another example, Applicant's copending Application No. 61/774,559 filed on Mar. 7, 2013, for an invention titled "METHOD AND SYSTEM FOR CLASSIFYING SOIL PRODUCTIVITY" provides a system for analyzing and using data collected from on-the-go soil EC and soil reflectance sensors. The contents of these prior applications are hereby incorporated herein by reference.

Soil EC relates to soil texture and soil moisture. Soil optical measurements relate to soil OM and soil moisture. Increasing levels of soil moisture increase soil's ability to conduct electricity and make the soil appear darker. The presence of soil moisture, especially when its variations do not spatially correlate with soil texture and soil OM, can confound soil EC and optical sensing of soil texture and soil OM. Soil EC and soil color sensors have been developed and are being used to relate to soil texture and organic matter, but no system or method exists for accounting for the contribution of soil moisture.

Typical planting depths for agricultural crops, such as corn, are 1.5 to 2.5 inches. The grower's objective is to place seed into warm, moist soil at a consistent depth to achieve uniform emergence. Germination and emergence are optimized when depth is consistent and seeds are placed in the optimal combination of warm and moist soil.

However, moisture and temperature vary spatially within fields and within the top 3 inches due to soil texture, topography, crop usage, irrigation patterns, residue cover, and a variety of other factors. Growers must occasionally compromise one factor for another, e.g., planting deeper into colder soil than desirable in order to have seed in moist soil.

There is a need for a method and system for on-the-go sensing of soil moisture, soil EC and other properties, and for using those measurements to improve various processes, such as variable rate irrigation, soil mapping, and planting.

SUMMARY OF THE INVENTION

A method and system for measuring multiple soil properties on-the-go is provided on an implement for traversing a field. An optical module is carried by the implement for collecting soil reflectance data. A pair of soil contact blades protrude from or are embedded in the optical module for collecting soil EC data and soil moisture data. A switching circuit or phase lock loop allows the same soil contact blades to feed signals to both a soil EC signal conditioning circuit and a soil moisture signal conditioning circuit. The soil moisture data can be used to calibrate the soil EC data and the soil reflectance data to compensate for effects of changing soil moisture conditions across a field. The system can also be used on a planter to control planting depth and/or seeding rate in real time based on multiple soil properties collected during planting.

According to one aspect of the present invention, an agricultural planter is provided, comprising: a planter row unit having a furrow opener for creating a furrow in which seeds are deposited; a sensor carried by the planter for measuring at least one soil property, the sensor comprising at least one of an optical module for collecting soil reflectance data, a soil EC measurement device for collecting soil EC data, a soil moisture measurement device for collecting soil moisture data, and a soil temperature measurement device for collecting soil temperature data; and a means for controlling a depth of operation of the furrow opener to control planting depth based on the at least one soil property measured by the sensor.

According to another aspect of the present invention, an agricultural planter is provided, comprising: a planter row unit having a furrow opener for creating a furrow in which seeds are deposited; a sensor carried by the planter for measuring at least one soil property, the sensor comprising at least one of an optical module for collecting soil reflectance data, a soil EC measurement device for collecting soil EC data, a soil moisture measurement device for collecting soil moisture data, and a soil temperature measurement device for collecting soil temperature data; and a depth control mechanism arranged to automatically vary a depth of operation of the furrow opener to adjust planting depth based on the at least one soil property measured by the sensor.

According to another aspect of the present invention, an agricultural planter is provided, comprising: a planter row unit having a furrow opener for creating a furrow in which seeds are deposited; an optical module for collecting soil reflectance data; a soil EC measurement device for collecting soil EC data; a soil moisture measurement device for collecting soil moisture data; and a means for varying a seeding rate of the planter on-the-go based on the data collected by the optical module, the soil EC measurement device and the soil moisture measurement device.

Numerous other objects of the present invention will be apparent to those skilled in this art from the following description wherein there is shown and described embodiments of the present invention, simply by way of illustration of some of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings.

In the drawings.

DETAILED DESCRIPTION OF THE INVENTION

A method and system for measuring multiple soil properties according to the present invention will now be described in detail with reference to FIGS. 1 to 12 of the accompanying drawings.

Figure 1:
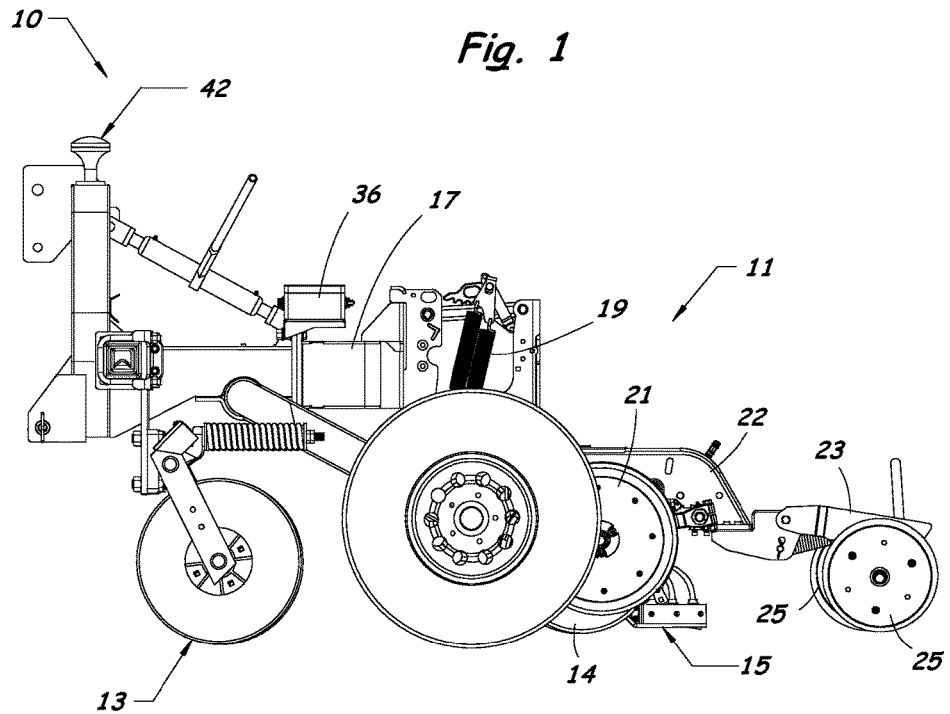
FIG. 1 is a side elevation view of an implement equipped with a system for measuring multiple soil properties according to the present invention.
Figure 2:
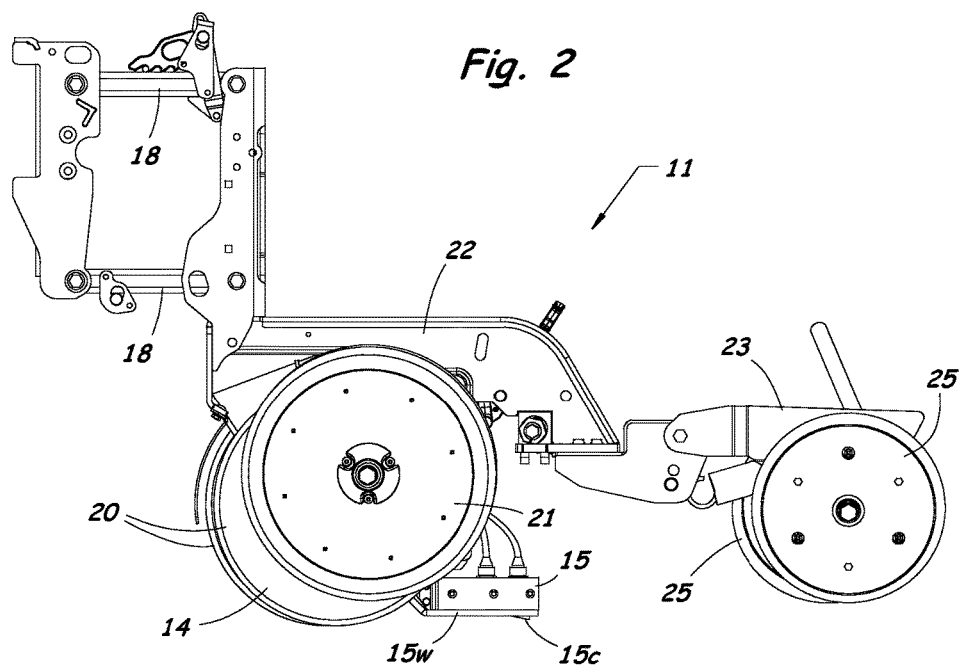
FIG. 2 is a side elevation view of a row unit of the implement shown in FIG. 1.
Figure 3:
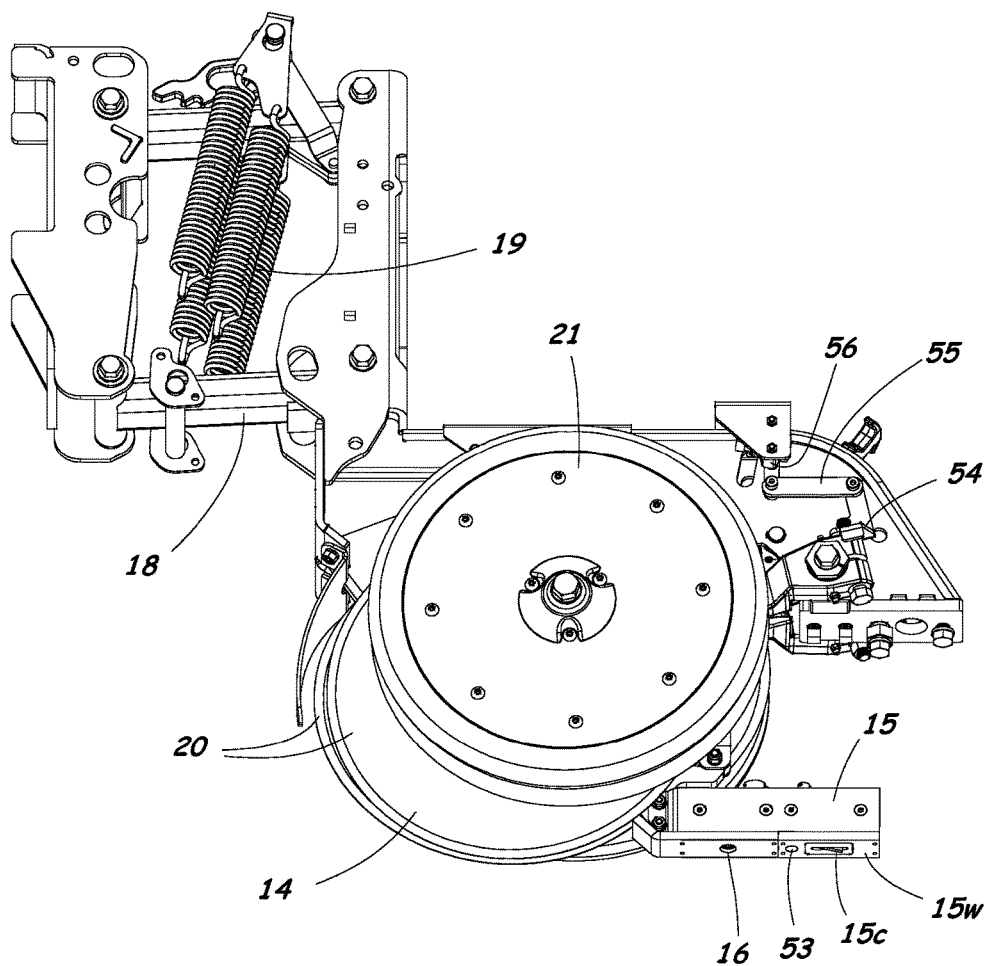
FIG. 3 is a lower left side perspective view of a row unit equipped with sensors for providing on-the-go measurements of soil moisture, soil EC, soil reflectance, and depth according to the present invention.

FIGS. 1 to 3 illustrate an implement 10 having a specially configured row unit 11 for measuring multiple soil properties according to the present invention. The implement 10 includes a coulter 13 for cutting through residue and for opening a slot in the soil. The row unit 11 includes a furrow opener assembly 14 that creates a furrow in the soil, and a sensor module 15 containing sensors for measuring multiple soil properties. The row unit 11 can be mounted to a toolbar 17 of the implement 10 by a parallel linkage 18 that allows the furrow opener 14 and sensor module 15 to follow ground undulations while maintaining a consistent depth in the soil. A plurality of springs 19 or a pneumatic system (not shown) can be used to provide an adjustable down-force to match soil conditions.

The furrow opener 14 in the illustrated embodiment includes two disks 20 that penetrate and follow in the slot created by the leading coulter 13. The disks 20 are arranged at a slight angle relative to a direction of travel so as to form a V-shaped slot or furrow in the soil. For example, the furrow opener 14 can be constructed in the same manner as a conventional double disk furrow opener used in an agricultural planter. Other types of furrow openers may also be used with the present invention.

A pair of gauge wheels 21 are mounted in close proximity to the furrow opener disks 20 to control the operating depth of the disks 20 and to scrape off any soil that adheres to the outer surfaces of the disks 20 during operation. The gauge wheels 21 are mounted together with the furrow opener disks 20 and the sensor module 15 on a subframe 22 of the row unit 11. The gauge wheels 21 maintain a consistent depth of the sensor module 15 in the soil during operation. For example, the gauge wheels 21 can be adjusted relative to the furrow opener disks 20 and sensor module 15 to allow measurements to be taken at selected depths of approximately 1 to 3 inches below the soil surface.

A furrow closing assembly 23 follows along behind the sensor module 15 to close the furrow after soil measurements are taken with the sensor module 15 to prevent erosion. The furrow closing assembly 23 can be a pair of closing wheels 25 as shown in FIGS. 1 and 2, or a pair of closing disks or other suitable closing members.

The sensor module 15 is mounted between the two furrow opener disks 20 and is pressed against the bottom of the furrow while measurements are being made. The sensor module 15 includes an optical module 15a at its front portion and a soil moisture and soil EC module 15b at its rear portion. The sensor module 15 has a hardened wear plate 15w on its bottom surface that presses against the soil within the furrow during operation. The wear plate 15w can be provided in two parts with a front part covering the bottom of the optical module 15a and a rear part covering the bottom of the soil moisture and soil EC module 15b. The front part of the wear plate 15w contains a sapphire window 16 for obtaining soil reflectance measurements. The consistent pressure of the sensor module 15 against the soil provides a self cleaning function that prevents a buildup of soil on the window 16.

Figure 4:
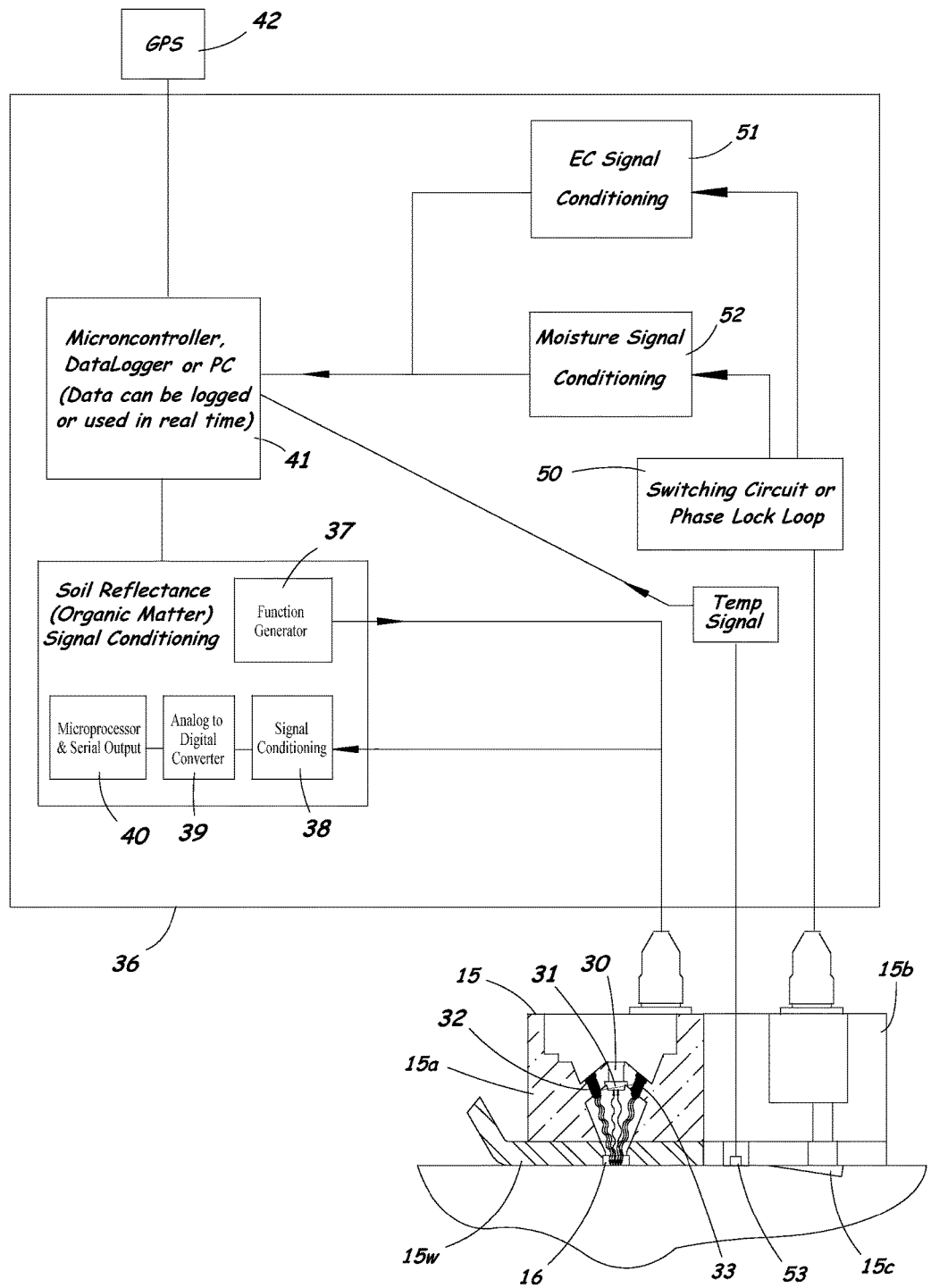
FIG. 4 is a diagram showing the basic circuit components of the system for measuring soil moisture, soil EC, and soil reflectance according to the present invention.
Figure 5:
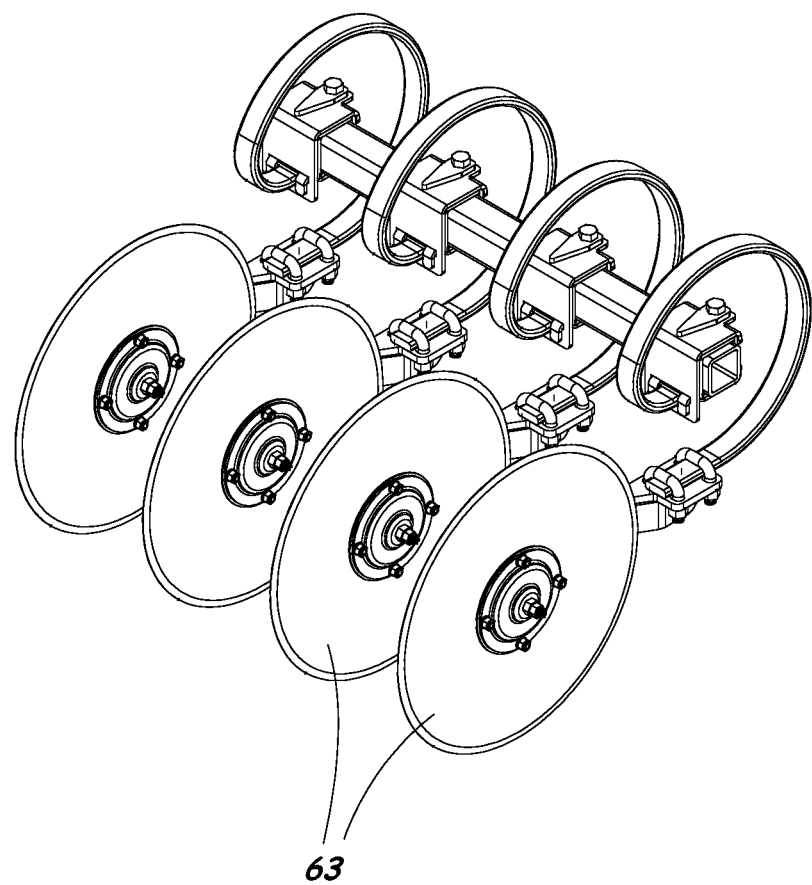
FIG. 5 is a perspective view of a group of rolling coulters that can be used to provide additional sets of soil contact members for collecting soil EC and soil moisture data.
Figure 6:
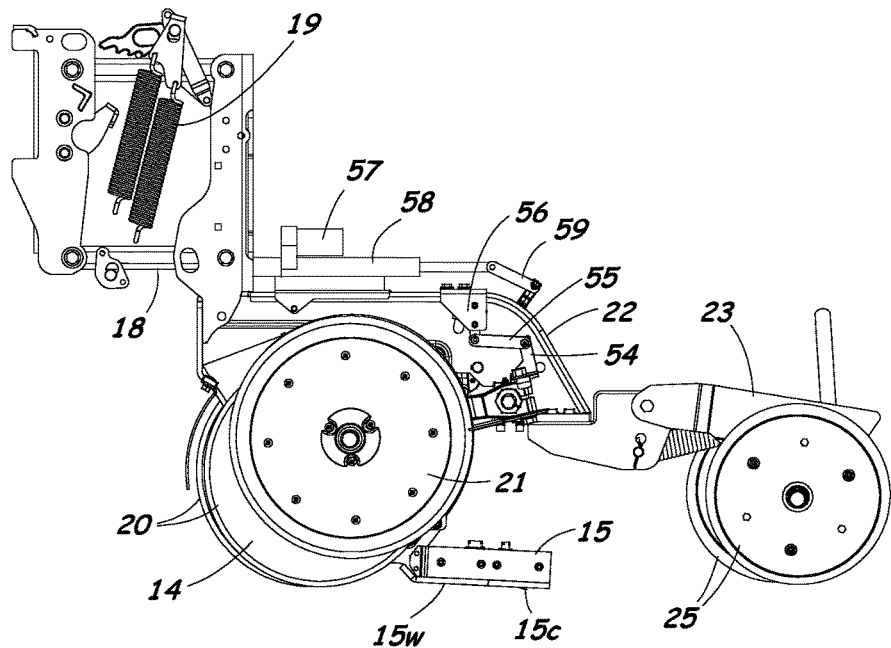
FIG. 6 is a side elevation view of a row unit equipped with a system for measuring multiple soil properties according to the present invention.

As illustrated in FIG. 4, the optical module 15a includes a single photodiode 30, a borosilicate photodiode protection window 31, two different wavelengths of modulating monochromatic light sources 32, 33 modulated at different frequencies, and the sapphire window 16 in the wear plate that presses against the soil within the furrow. The modulated light is directed from the two light sources 32, 33 through the sapphire window 16 onto the soil. The reflected light is then received by the photodiode 30, converted to a modulated voltage, and sent to a signal conditioning circuit 38 in the controller 36. The photodiode 30 is hermetically sealed with the borosilicate window 31 protecting the surface. This allows for easy cleaning and is robust for outdoor use.

The controller 36 includes two function generators 37 for generating the modulated light from the two light sources 32, 33, the signal conditioning circuit 38 including a phase lock loop (PLL) to separate each source of reflected light from the photodiode signal, an analog to digital (A/D) converter 39, and a serial output 40 for data logging.

The function generators 37 send two separate pulses; one goes to the first wavelength light-emitting diode (LED) 32, the other to the second wavelength LED 33. These pulses are directed at the soil through the sapphire window 16. The light reflected off the soil is read by the photodiode 30 and converted into a modulated voltage. The modulated voltage from the photodiode 30 is processed through the signal conditioning circuit 38, which converts the modulated voltage to a DC voltage. The DC voltage is processed through the A/D converter 39, then the output is sent through the serial output 40 to the DataLogger or PC 41. The data is georeferenced using a GPS signal from a GPS receiver 42 connected to the DataLogger or PC 41.

By modulating the LEDs 32, 33 at two separate known frequencies and sending the modulated photodiode voltage to the PLL 38, each LED signal can be extracted individually from the photodiode signal, without receiving interference from the other LED light source or ambient light. This allows for a clean signal of only the reflected light of each LED to be stored, free from any outside interference.

Correlating sensor data to soil properties requires the development of calibration equations. Previous calibration attempts with simple optical devices have relied on bivariate regression, with the optical data as the sole sensor variable. One of the situations that can confound optical measurements of organic matter is soil moisture that relates to soil texture variations in addition to relating to organic matter variations.

The present invention includes the use of soil contacting members 15c for collecting soil EC and soil moisture data in close proximity and at approximately the same depth as the optical module 15a. The soil contacting members 15c can protrude from the sensor module 15, or the soil contacting members 15c can be embedded in poly or other non-conductive material so that they are flush with an outer surface of the sensor module 15b. The soil contacting members 15c can be a pair of soil contacting blades, as in the illustrated embodiment, or there can be more than two (e.g., 3 or 4) soil contacting surfaces on the sensor module 15 or blades protruding from the sensor module 15. The soil contacting members 15c can also be a single soil contacting blade in combination with the metal housing of the sensor module 15 serving as the other soil contacting member. The soil contact members 15c are preferably arranged so that they are pressed into or against the soil to make good soil contact.

In the illustrated embodiment, the soil contacting members 15c comprise a pair of spaced apart metal blades that protrude downwardly from the bottom surface of the rear part of the wear plate 15w. The soil contacting members 15c are pressed into or against the soil to measure the soil EC and soil moisture at approximately the same depth as the soil reflectance measurements are collected by the optical module 15a as the implement 10 travels across the field.

Soil EC has been proven to correlate well with soil texture. Soil EC and soil reflectance data can be used together to help resolve organic matter variations in the field. However, both soil EC and soil optical measurements are affected by soil moisture; increased soil moisture causes higher EC conductance and reduces optical reflectance. Soil moisture typically varies spatially within a field and with depth. In dry conditions, the moisture increases with depth; however following a precipitation event the opposite may be true. In order to improve calibrations to soil texture and cation exchange capacity (CEC), which typically correlate to soil EC, effects of moisture need to be accounted for. Similarly, soil OM predictions from optical sensors can be improved by accounting for soil moisture. In the present invention, soil moisture data is used by the controller 36 to calibrate the soil EC and soil reflectance measurements to account for the effect of soil moisture variations on the soil EC and soil reflectance data.

The soil contacting members 15c are used to collect both soil EC and soil moisture data. In one embodiment, a switching circuit 50 is connected to the soil contact members for automatically switching back and forth between a soil EC conditioning circuit 51 and a soil moisture conditioning circuit 52. The soil EC conditioning circuit 51 may comprise, for example, dipole circuitry, while the soil moisture conditioning circuit 52 may comprise, for example, capacitance circuitry using frequency domain reflectometry (FDR) measurement. The switching circuit 50 allows both soil EC and soil moisture readings to be collected from the same soil contact members 15c. The switching circuit 50 can be set to switch back and forth rapidly between the soil EC and soil moisture conditioning circuits to collect both soil EC and soil moisture readings virtually simultaneously.

Other circuit arrangements can be made to collect both soil EC and soil moisture data from the soil contact members 15c. For example, a phase lock loop can be connected to the soil contact members 15c for capturing both soil EC and soil moisture readings simultaneously.

The soil contact members 15c on the bottom of the wear plate 15w are most suitable for contacting the soil at a shallow depth, e.g., 1 to 3 inches. One or more additional sets of soil contact members (not shown) can be used to make soil EC measurements on a separate circuit from the first set of soil contact members 15c. In this case, the first set of soil contact members 15c can be used to collect soil moisture measurements, and the second set of soil contact members can be used to collect soil EC measurements. In this configuration, the soil moisture contact members 15c are on a separate circuit from the soil EC contact members, and there is no need for the switching circuit or phase lock loop 50.

Additional sets of soil contact members can also be added to the implement 10 to collect soil EC and soil moisture data from different depths. For example, multiple sets of metal blades, such as rolling coulter blades 63 (FIG. 5), can be arranged on the implement 10 to contact the soil at a greater depth than the first set of soil contact members 15c to collect soil EC and soil moisture readings from multiple depths as the implement 10 traverses the field.

A soil temperature sensing device 53 is also arranged in the sensor module 15. The soil temperature sensing device 53 may include, for example, a thermocouple or infrared temperature sensor positioned in or on the wear plate 15w of the sensor module. The temperature sensing device 53 is preferably arranged to collect soil temperature data from the soil at approximately the same depth as the soil EC and soil moisture data are collected. Soil EC values increase with increased soil temperature, so accounting for temperature variations can improve calibrations to soil texture and soil CEC. Soil temperature can also be used in conjunction with a system for on-to-go sensing of soil properties during planting, as further explained below.

The sensor row unit 11 includes a means for monitoring and controlling a depth of operation of the furrow opener 14. This means includes a depth sensor gauge wheel mount 54, a mechanical depth sensor linkage 55, and a depth sensor 56. The depth sensor 56 can be, for example, an optical encoder or a rotary or linear potentiometer sensor that provides a signal to the controller 36 based on the angle of rotation of the sensor linkage 55. The sensor row unit 11 can also include an adjustable downpres sure system or a remote depth adjustment mechanism 57 (FIG. 6) to vary the operating depth of the furrow opener 14 to adjust the depth of soil measurements. In the illustrated embodiment, the depth adjustment mechanism 57 includes an actuator 58 and linkage 59 coupled to an adjustment arm on the planter row unit 61.

As the sensor row unit 11 moves through the field, undulations and soil clods may cause the row unit depth 11 to vary. The depth sensor 56 records the depth at which all optical, EC and moisture measurements are collected, which allows these measurements to be evaluated and erroneous ones removed.

The data received from the optical measurement device 15a, the soil EC measurement device 15c, 51, the soil moisture measurement device 15c, 52, the soil temperature measurement device 53, and the soil depth measurement device 56 are all georeferenced using the GPS signal from the GPS receiver 42 connected to the DataLogger or PC 41. Each data point will include a latitude/longitude value, a sensor operating depth, and the sensor values. The controller 36 is programmed to create a georeferenced map of these data points for multiple soil properties as the implement 10 traverses the field and collects the data. The controller 36 can also be programmed to automatically cycle the sensor row unit 11 to vary the depth of operation of the sensor module 15 on-the-go. This will allow one sensor row unit 11 containing the sensor module 15 to collect dense data of multiple soil properties at multiple, discrete depths. This will also improve estimations of soil OM because the calibrations would include sensor readings from multiple depths.

The depth sensor 56, depth adjustment mechanism 57, and depth cycling feature of this invention can be used for all of the sensors (e.g., optical, EC, moisture, and temperature) carried by the sensor module 15. Alternatively, the depth sensor and depth cycling feature could be used for any one of these sensors individually. For example, an implement having an optical module with an optical sensor (with or without the other sensors) would benefit from having the depth sensor and depth cycling feature, which would improve quality control and provide additional reflectance data at multiple depths for analysis. Similarly, an implement having a soil EC sensor and/or a soil moisture sensor could be equipped with the depth sensor and depth cycling feature of the present invention.

The controller 36 can also include an algorithm to determine available water holding capacity of the soil based on the measured soil EC, soil reflectance, and soil moisture. The water holding capacity will provide a useful measure for scheduling irrigation, and particularly for variable rate irrigation in fields with large spatial variations in water holding capacity. The water holding capacity will also provide a useful metric for varying seeding population because water holding capacity can be a good indicator of soil productivity. Linking moisture sensing with sensors that relate to soil texture and organic matter, which affect water-holding capacity and crop usage of water, will provide additional synergistic information that individual moisture sensors are unable to do alone.

An agricultural planter 60 equipped with the system for measuring multiple soil properties will now be described with reference to FIGS. 7 to 12. The planter 60 includes at least one planter row unit 61 having a furrow opener 14 for creating a furrow, and a seed metering mechanism 62 for singulating and depositing seeds through a seed tube T into the furrow. The planter row unit 61 includes depth gauge wheels 21 that control a depth of operation of the furrow opener 14.

The planter row unit 61 includes a means for monitoring and controlling a depth of operation of the furrow opener 14. This means includes a depth sensor gauge wheel mount 54, a mechanical depth sensor linkage 55, and a depth sensor 56. The depth sensor 56 can be, for example, an encoder that provides a signal to the controller 36 based on the angle of rotation of the sensor linkage 55.

The planter row unit 61 can also include an adjustable downpressure system or a remote depth adjustment mechanism to vary the operating depth of the furrow opener 14 to adjust the planting depth. For example, the remote depth adjustment mechanism 57 illustrated in FIG. 7 includes a linear actuator 58 and linkage 59 coupled to the existing adjustment arm on the planter row unit 61. The actuator 58 can be powered by a hydraulic, pneumatic, or electrical system.

The planter row unit 61 includes a system for measuring multiple soil properties on-the-go as the planter traverses a field. This system includes, among other things, a soil moisture measurement device 15c for collecting soil moisture data from soil in the field at various depths, and a soil temperature measurement device 53 for collecting soil temperature data from the soil at various depths (see FIG. 4). These measurement devices will provide growers with precise information about the soil moisture and soil temperature within their seedbeds in order to make better planting decisions and adjustments. For example, the information may be used to provide real-time adjustments of planting depth, and/or to make sure that the planting depth is consistent and optimal for germination and emergence.

The soil moisture measurement device 15c and soil temperature measurement device 53 are both carried by the sensor module 15, as described above. The sensor module 15 also includes a soil EC measurement device 15c, and an optical module 15a for measuring soil OM. The other parts of the planter row unit 61 having the same construction as the system 10 described above are depicted in FIG. 7 with the same reference numerals.

Figure 7:
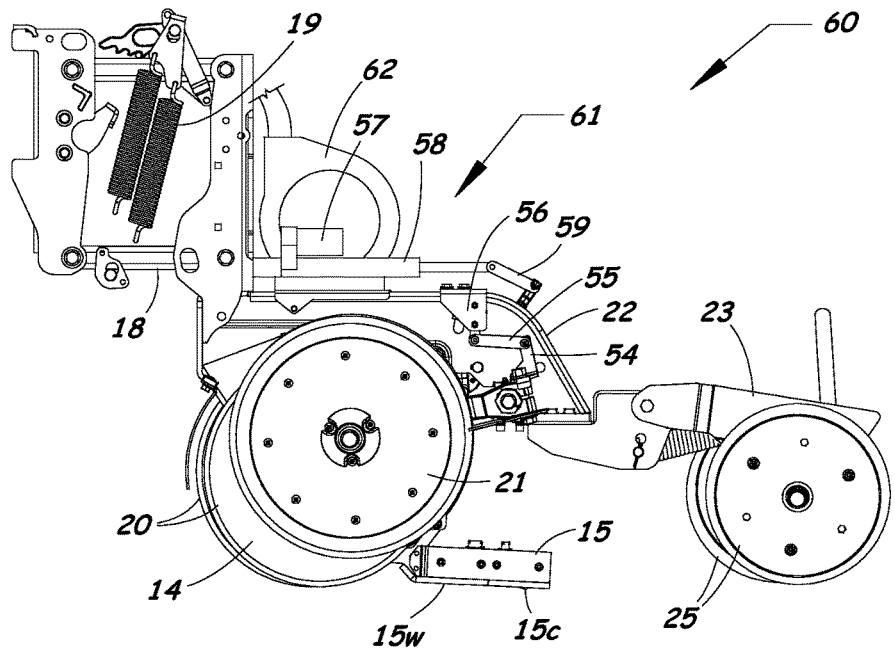
FIG. 7 is a side elevation view of a planter row unit equipped with a system for measuring multiple soil properties for use in adjusting planting depth and/or seeding rate in real time according to the present invention.

As illustrated in FIG. 7, the sensor module 15 follows behind the furrow opener 14 and also behind where seeds are dropped from the seed tube T into the furrow created by the furrow opener 14. The sensor module 15 slides across the bottom of the furrow and presses the planted seeds into the bottom of the furrow, while at the same time collecting soil measurements. This allows the sensor module 15 to function as a seed firmer as well as a means for measuring soil properties.

Figure 8:
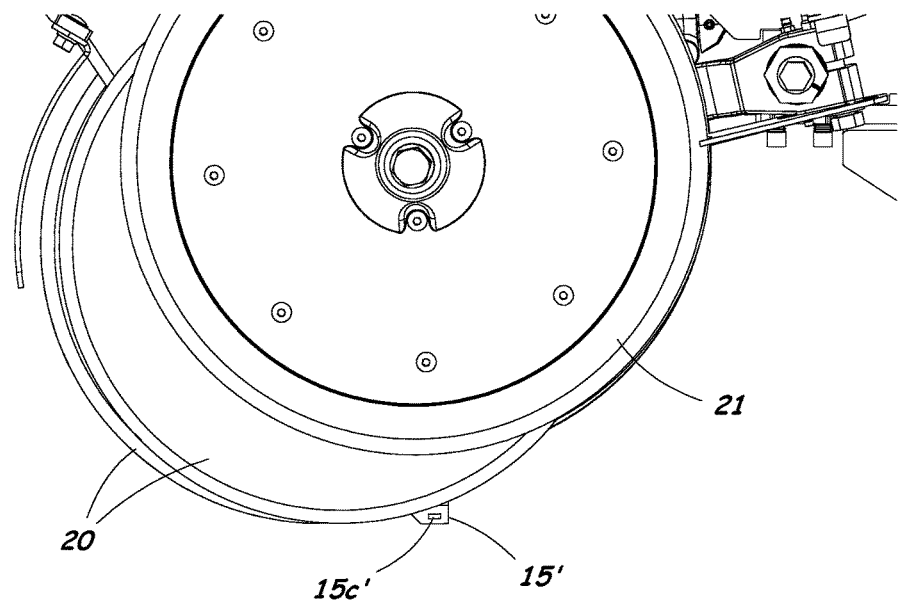
FIG. 8 is a side elevation view of a furrow opener assembly of a planter row unit having a sensor module combined with a seed tube guard located between the furrow opener disks.
Figure 9:
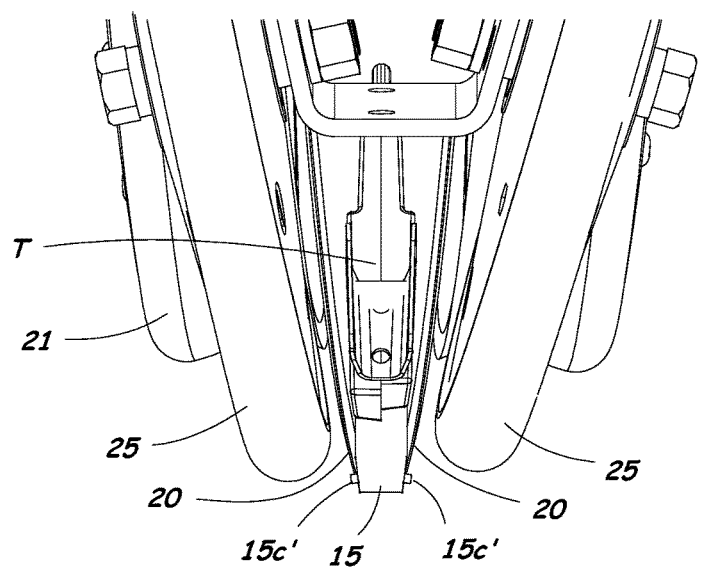
FIG. 9 is a rear elevation view of the furrow opener assembly shown in FIG. 7.
Figure 10:
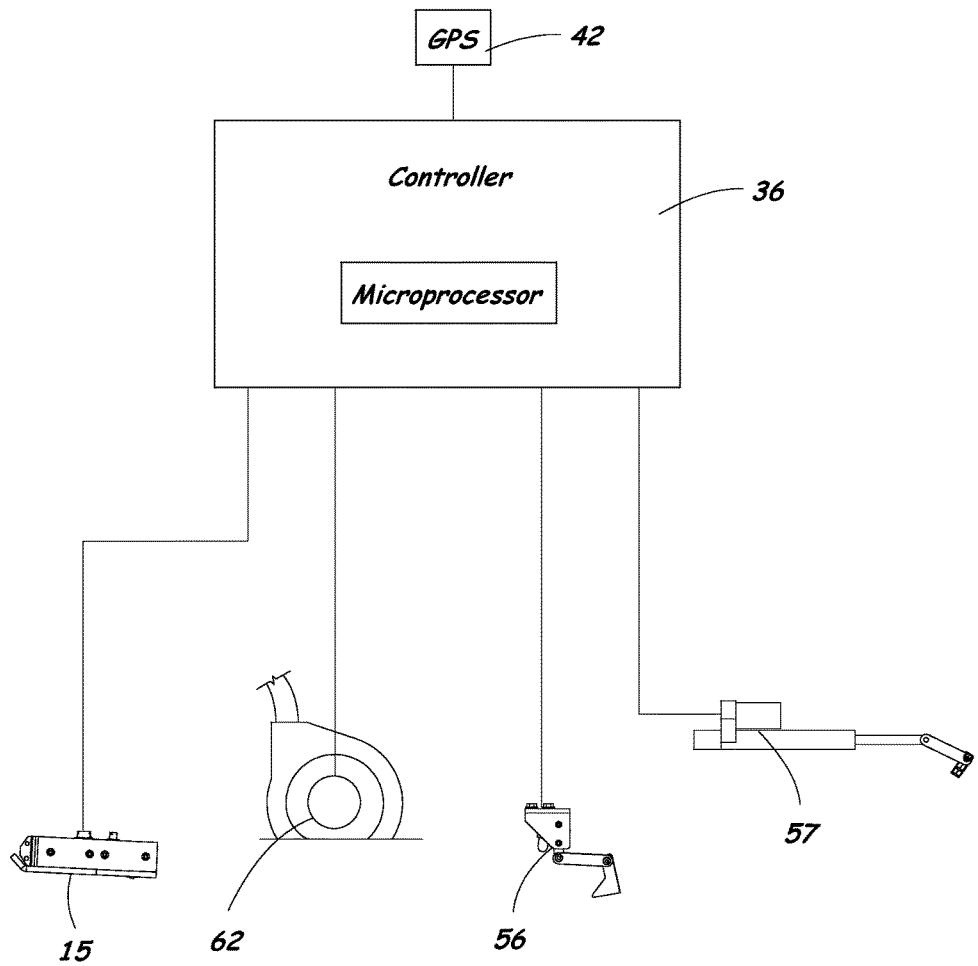
FIG. 10 is a diagram of a control system for an agricultural planter for varying seeding rate and planting depth based on soil properties measured by sensors carried by the planter.

FIGS. 8 and 9 illustrate another embodiment in which a sensor module 15' containing a soil moisture and EC measurement device 15c' and the optical module is mounted between the furrow opener disks 20 so as to be positioned in front of the seed tube T that drops seeds into the furrow. In this embodiment, the sensor module 15' is formed as part of a seed tube guard located between the furrow opener disks 20 immediately forward of the seed tube T. This arrangement allows the sensor module 15' to collect its measurements from the soil at the bottom or sides of the furrow without disturbing the seed placement.

Figure 11:
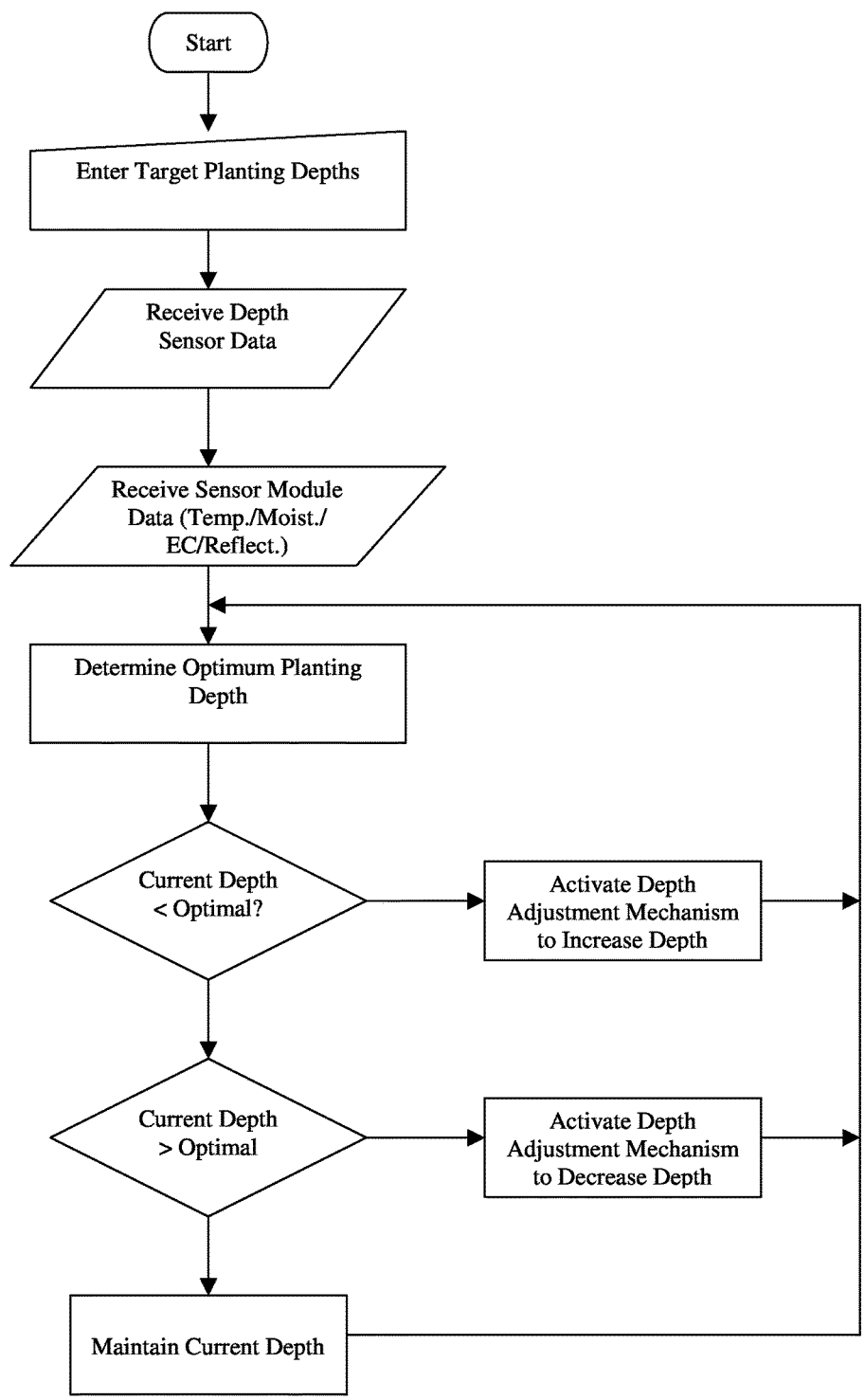
FIG. 11 is a flowchart of an algorithm used by the control system for varying planting depth.

FIG. 11 illustrates an algorithm used by the controller 36 to control planting depth on-the-go during planting operations. The user can input target planting depths that will be used by the system for various predetermined soil conditions, or the system can be programmed to determine optimum planting depths based on various measured soil properties. The controller 36 receives planting depth data from the depth sensor 56 and soil moisture data, soil OM data, soil EC data, and soil temperature data from the sensor module 15. The controller 36 uses this data to determine the optimum planting depth in real time at the current location. The controller 36 will then compare the calculated optimum planting depth to the current depth measured by the depth sensor 56 and activate the depth adjustment mechanism 57 to raise or lower the furrow opener 14 to cause the planter to plant at the optimum depth.

For example, when the soil moisture is determined to be insufficient for planting at a very shallow depth, the controller 36 will cause the furrow opener 14 to operate at a greater depth to increase the planting depth for planting in moist soil. For another example, when the soil temperature is determined to be too cold at a relatively deep planting depth, the controller 36 will cause the furrow opener 14 to operate at a shallower depth to decrease the planting depth for planting in warmer soil. The controller 36 will use an algorithm with predetermined parameters to automatically achieve an optimum planting depth in real time based on the soil moisture, soil OM, soil texture, and/or soil temperature data collected during the planting process.

Figure 12:
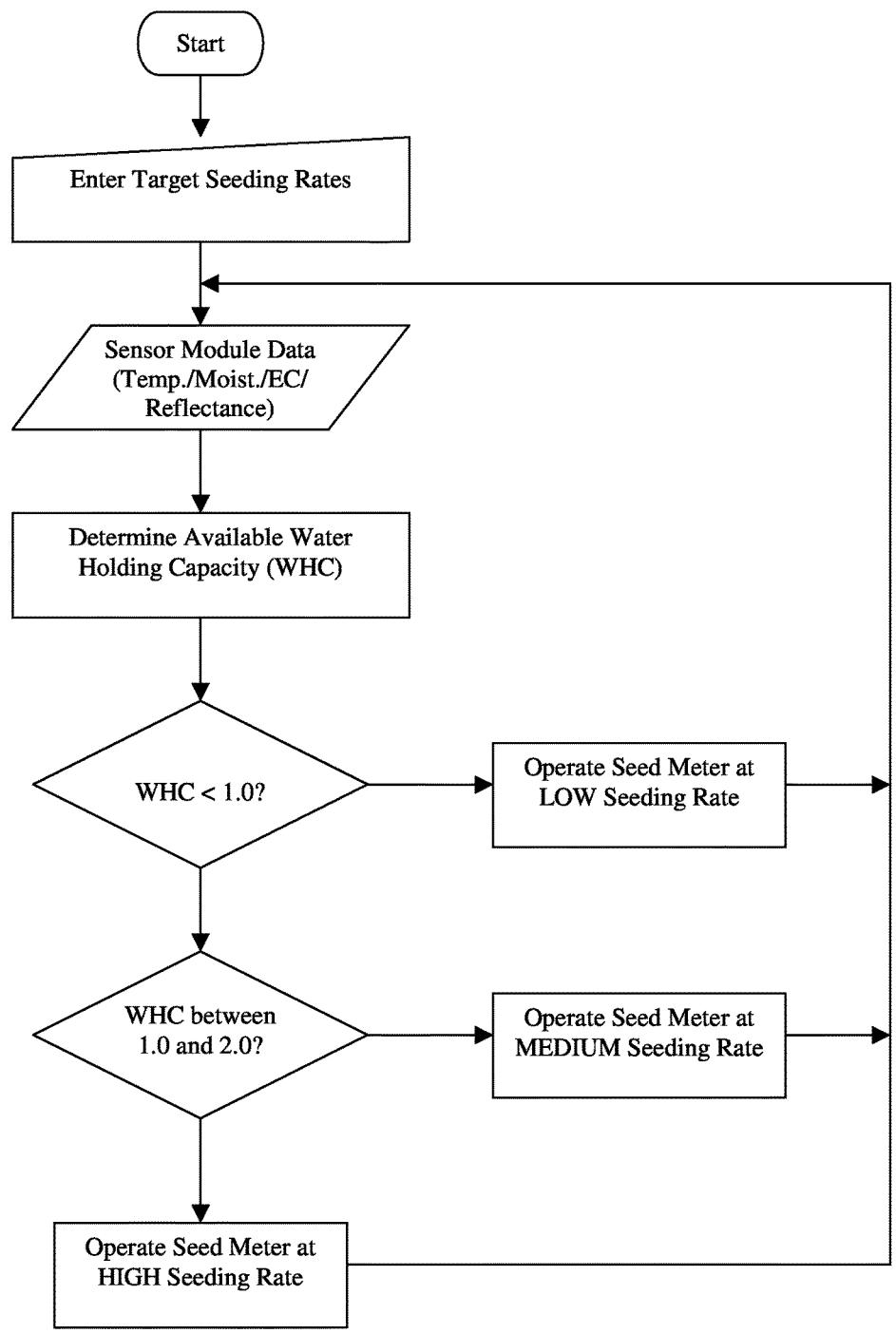
FIG. 12 is a flowchart of an algorithm used by the control system for varying seeding rate.

FIG. 12 illustrates an algorithm used by the controller 36 on the planter 60 for varying seeding rate of the planter on-the-go based on the data collected by the sensor module 15. For example, the controller 36 can be programmed with an algorithm or lookup table to determine available water holding capacity of the soil based on the measured soil EC, soil reflectance, and soil moisture. The available water holding capacity will provide a useful measure for soil productivity, and can be used to vary the seeding rate of the planter 60. The controller 36 can control the seed metering mechanism 62 on-the-go during planting to increase the seeding rate when the algorithm determines that the available water holding capacity of the soil is relatively high, and to decrease the seeding rate when the algorithm determines that the available water holding capacity of the soil is relatively low. For example, coarse soils having a water holding capacity of less than 1.0 inches of water per foot of soil may be known to be less productive in some areas, and the controller 36 can be set to decrease the seeding rate when such soil conditions are detected. On the other hand, fine soils having a water holding capacity of greater than 2.0 inches of water per foot of soil may be determined to be the most productive soils, so the controller 36 can be set to increase the seeding rate when such soil conditions are detected. Measures of soil productivity other than water holding capacity can also be used as a basis for varying the seeding rate.

The system for measuring multiple soil properties of the present invention provides significant advantages and improvements over existing systems. Measuring soil moisture, soil EC, and soil reflectance at the same spatial locations and depths as the implement traverses the field will reveal additional information and increase the value of each sensor and the information it provides.

While the invention has been described in connection with specific embodiments thereof, it is to be understood that this is by way of illustration and not of limitation, and the scope of the appended claims should be construed as broadly as the prior art will permit.

What is claimed is:

1. An agricultural planter comprising:
   a planter row unit having a furrow opener for creating a furrow in which seeds are deposited;
   a sensor carried by the agricultural planter for measuring at least one soil property, said sensor comprising at least one of an optical module for collecting soil reflectance data, a soil EC measurement device for collecting soil EC data, a soil moisture measurement device for collecting soil moisture data, and a soil temperature measurement device for collecting soil temperature data; and
   a means for controlling a depth of operation of said furrow opener to control planting depth based on said at least one soil property measured by said sensor;
   wherein said means for controlling a depth of operation of said furrow opener comprises an automatic adjustment means for adjusting a depth of the furrow opener in real time based on said at least one soil property measured by said sensor.

2. The agricultural planter according to claim 1, wherein said sensor is an optical module for collecting soil reflectance data.

3. The agricultural planter according to claim 1, wherein said sensor is a soil EC measurement device, and wherein said at least one soil property comprises soil EC.

4. The agricultural planter according to claim 1, wherein said sensor is a soil moisture measurement device, and wherein said at least one soil property comprises soil moisture.

5. The agricultural planter according to claim 1, wherein said sensor is a soil temperature measurement device, and wherein said at least one soil property comprises soil temperature.

6. The agricultural planter according to claim 1, wherein said sensor comprises a soil moisture measurement device and a soil temperature measurement device for measuring soil moisture and soil temperature, respectively, and wherein said automatic adjustment means for adjusting a depth of the furrow opener in real time uses an algorithm that determines optimum planting depth based on soil moisture and soil temperature.

7. The agricultural planter according to claim 1, further comprising a means for adjusting a depth of operation of said sensor on-the-go for measuring said at least one soil property at various depths in the soil.

8. The agricultural planter according to claim 7, wherein said means for adjusting a depth of operation of said sensor comprises a means for adjusting an operating depth of said sensor on-the-go to multiple operating depths to measure said at least one soil property at multiple discrete depths.

9. The agricultural planter according to claim 1, wherein said sensor comprises a sensor module assembly comprising an optical module for collecting soil reflectance data, a soil EC measurement device for collecting soil EC, a soil moisture measurement device for measuring soil moisture, and a soil temperature measurement device for measuring soil temperature.

10. An agricultural planter comprising:
    a planter row unit having a furrow opener for creating a furrow in which seeds are deposited;

a sensor carried by the agricultural planter for measuring at least one soil property, said sensor comprising at least one of an optical module for collecting soil reflectance data, a soil EC measurement device for collecting soil EC data, a soil moisture measurement device for collecting soil moisture data, and a soil temperature measurement device for collecting soil temperature data; and a depth control mechanism arranged to automatically vary a depth of operation of said furrow opener to adjust planting depth in real time based on said at least one soil property measured by said sensor.

11. The agricultural planter according to claim 10, further comprising a seed firmer for firming seeds into soil in the furrow created by the furrow opener, and wherein said sensor is located on said seed firmer.

12. The agricultural planter according to claim 10, wherein said furrow opener comprises a pair of opener disks, and said row unit further comprises a seed tube and a seed tube guard positioned between said opener disks, said seed tube guard being positioned in front of said seed tube, and wherein said sensor is located on said seed tube guard.

13. The agricultural planter according to claim 10, wherein said sensor is an optical module for collecting soil reflectance data.

14. The agricultural planter according to claim 10, wherein said sensor is a soil EC measurement device, and wherein said at least one soil property comprises soil EC.

15. The agricultural planter according to claim 10, wherein said sensor is a soil moisture measurement device, and wherein said at least one soil property comprises soil moisture.

16. The agricultural planter according to claim 10, wherein said sensor is a soil temperature measurement device, and wherein said at least one soil property comprises soil temperature.

17. The agricultural planter according to claim 10, wherein said sensor comprises a soil moisture measurement device and a soil temperature measurement device for measuring soil moisture and soil temperature, respectively, and wherein said depth control mechanism automatically adjusts a depth of the furrow opener during operation based on soil moisture and soil temperature.

18. The agricultural planter according to claim 10, wherein said sensor comprises a sensor module assembly comprising an optical module for collecting soil reflectance data, a soil EC measurement device for collecting soil EC, a soil moisture measurement device for measuring soil moisture, and a soil temperature measurement device for measuring soil temperature.

* * * * *